US00PP26088P2

(12) United States Plant Patent
Spek

(10) Patent No.: US PP26,088 P2
(45) Date of Patent: Nov. 17, 2015

(54) ***ILEX* PLANT NAMED 'SPEK 02'**

(50) Latin Name: *Ilex aquifolium*
Varietal Denomination: Spek 02

(71) Applicant: Pieter Spek, Boskoop (NL)

(72) Inventor: Pieter Spek, Boskoop (NL)

(73) Assignee: JOH. SPEK BOOMKWEKERIJEN B.V., Boskoop (NL)

( * ) Notice: Subject to any disclaimer, the term of this patent is extended or adjusted under 35 U.S.C. 154(b) by 180 days.

(21) Appl. No.: 13/987,366

(22) Filed: Jul. 17, 2013

(51) Int. Cl.
*A01H 5/12* (2006.01)

(52) U.S. Cl.
USPC ..... Plt./247

(58) Field of Classification Search
USPC ..... Plt./247
See application file for complete search history.

(56) References Cited

PUBLICATIONS

Upov Pluto Plant Variety Database 20150316, retrieved on Mar. 16, 2015, retrieved from the Internet at <http://www.upov.int/pluto/en/index.jsp> for Ilex 'Red Tips' one page.*

* cited by examiner

*Primary Examiner* — June Hwu
(74) *Attorney, Agent, or Firm* — Penny J. Aguirre

(57) ABSTRACT

A new cultivar of *Ilex aquifolium,* 'Spek 02', that is characterized by its variegated foliage with deep green centers and golden yellow margins, its deep purple-red young shoots, its good winter hardiness, and its ability to be readily propagated by softwood stem cuttings.

2 Drawing Sheets

Botanical classification: *Ilex aquifolium.*
Variety denomination: 'Spek 02'.

BACKGROUND OF THE INVENTION

The present invention relates to a new and distinct cultivar of *Ilex aquifolium* and will be referred to hereafter by its cultivar name, 'Spek 02'. 'Spek 02' is a new cultivar of holly grown for use as a landscape plant.

The Inventor discovered the new cultivar in November of 2001 as a naturally occurring branch mutation of an unnamed plant of *Ilex aquifolium* from his breeding program that was growing in a field plot in Boskoop, The Netherlands.

Asexual propagation of the new cultivar was first accomplished by the Inventor using softwood stem cuttings in June of 2002 in Boskoop, The Netherlands. Asexual propagation by softwood stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'Spek 02' as a unique cultivar of *Ilex.*

1. 'Spek 02' exhibits variegated foliage with deep green centers and golden yellow margins.
2. 'Spek 02' exhibits deep purple-red young shoots.
3. 'Spek 02' exhibits good winter hardiness; hardy at least in U.S.D.A. Zone 6.
4. 'Spek 02' is readily propagated by softwood stem cuttings.

The parent plant, an unnamed plant of *Ilex aquifolium,* differs from 'Spek 02' in having green non-variegated leaves, new shoots that are less intense in color, and in having less branching. 'Spek 02' can be most closely compared to the cultivars 'Madame Briot' (not patented) and 'Golden Queen' (not patented). Both are similar to 'Spek 02' in having foliage that is vareigated with golden yellow margins. 'Madame Briot' differs from 'Spek 02' in having young shoots that are less intense purple-red in color, in having less winter hardiness, in being less freely branched and in being more difficult to propagate. 'Golden Queen' differs from 'Spek 02' in having young shoots that are just slightly purple-red in color, in having less winter hardiness, in having leaves that are less sharply toothed and in being more difficult to propagate.

BRIEF DESCRIPTION OF THE DRAWINGS

The accompanying colored photographs illustrate the overall appearance and distinct characteristics of an 18 month-old plant of the new cultivar field as grown outdoors in a 13 cm container in Boskoop, The Netherlands and placed in a container for the photographs.

The photograph in FIG. 1 provides a side view of a plant of 'Spek 02'.

Figure 1:
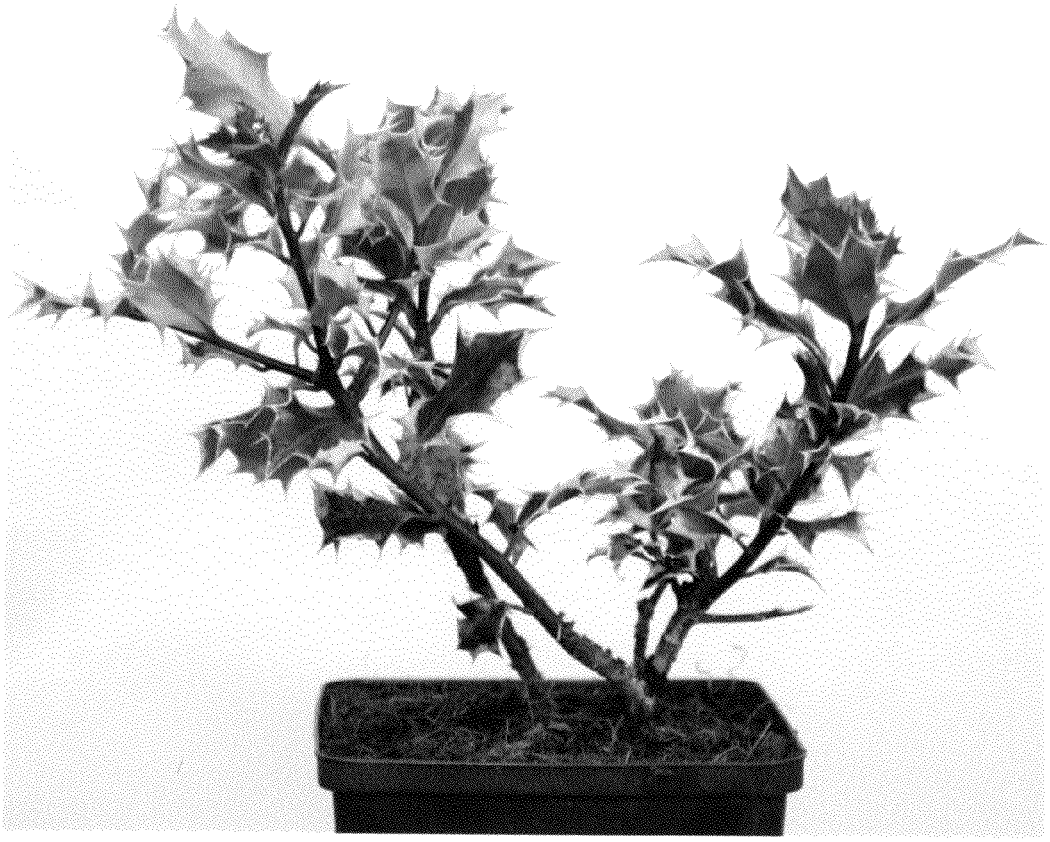
Figure 2:
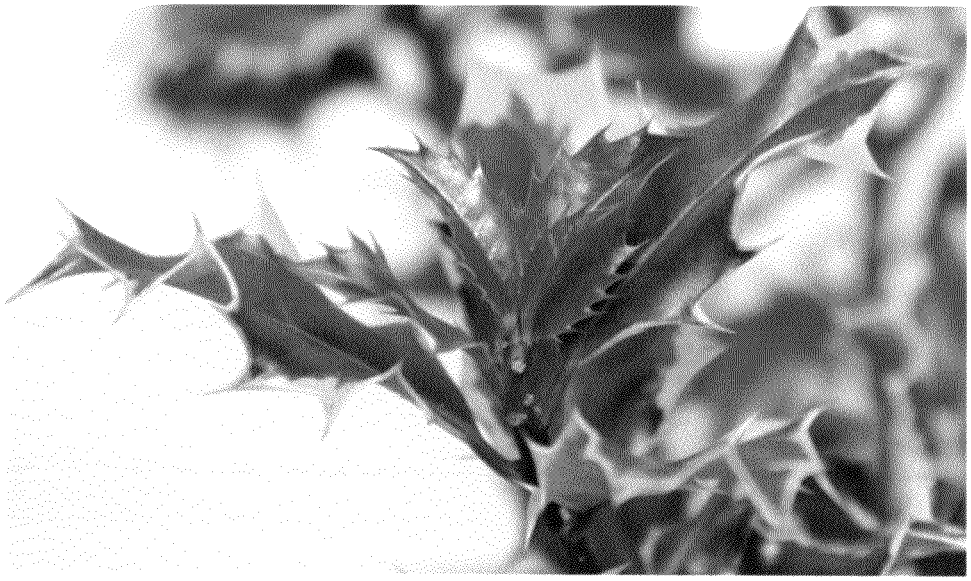

The photograph in FIG. 2 provides a close-up view of the new foliage of 'Spek 02'.

Figure 3:
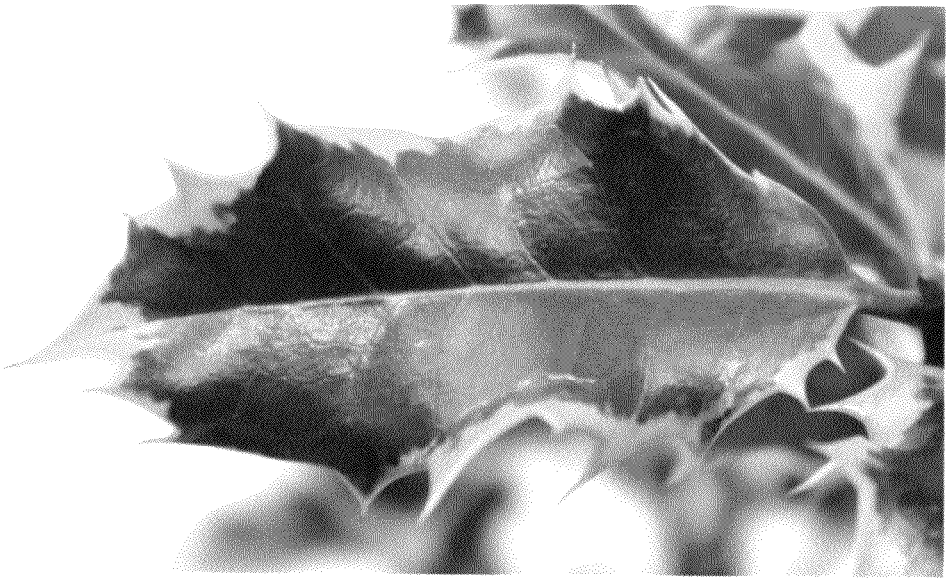

The photograph in FIG. 3 provides a close-up view of the mature foliage of 'Spek 02'.

The colors in the photographs may differ slightly from the color values cited in the detailed botanical description, which accurately describe the colors of the new *Ilex.*

DETAILED BOTANICAL DESCRIPTION

The following is a detailed description of 18 month-old plants of the new cultivar as grown outdoors in a 13-cm container in Boskoop, The Netherlands. Plants were grown under average day temperatures of 9° to 20° C. and average night temperatures of 1° to 13° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Evergreen shrub.

*Plant habit*.—Broad upright plant habit.

*Height and spread*.—Reaches about 18.1 cm in height and 22.2 cm in spread on a 1.5 year-old plant, matures to 3 m in height and 2 m in width in the landscape.

*Cold hardiness*.—At least in U.S.D.A Zone 6.

*Diseases resistance*.—Not more susceptible to pests and diseases than other *Ilex aquifolium*.

*Root description*.—Slightly fibrous, 161A in color.

*Propagation*.—Softwood stem cuttings.

*Growth rate*.—Moderately vigorous.

Stem description:

*Shapes*.—Rounded.

*Stem color*.—Young stem; a color between N186C and 200A, mature wood; 147A.

*Stem size*.—Lateral branches are 6 cm in length and 2 mm in diameter.

*Stem surface*.—Smooth and slightly glossy.

*Internode length*.—An average of 0.9 cm.

*Branching*.—Free branching, average of 8 lateral branches.

Foliage description:

*Leaf shape*.—Ovate to elliptic.

*Leaf division*.—Simple.

*Leaf base*.—Very short attenuate to rounded.

*Leaf apex*.—Sharp acuminate, curved downward.

*Leaf fragrance*.—None.

*Leaf venation*.—Pinnate, 144A to 144B in color on upper surface, 176A to 176B in color on lower surface.

*Leaf margins*.—Undulate and deeply spinose, average of 18 spines per leaf (9 on each side).

*Leaf arrangement*.—Alternate.

*Leaf aspect*.—Held slightly upwards.

*Leaf attachment*.—Petiolate.

*Leaf surface*.—Glabrous, thick and leathery on both surfaces, upper surface very glossy, lower surface slightly glossy.

*Leaf size*.—Average of 4.7 cm in length and 3 cm in width.

*Leaf quantity*.—Numerous, average of 8 per branch.

*Leaf color*.—Young upper surface; ranges from 183A to 183B to a color between N186C and 200B, young lower surface; a color between 174A and N186C, mature upper surface; a color between N137A and 147A, margins and spines a color between 6A and 12A, mature lower surface; 146D, margins and spines a color between 2B and 8A.

*Petioles*.—An average of 5 mm in length and 2 mm in width, color; upper side N186C, lower side 176A, surface is glabrous.

*Leaf spines*.—Not very sharp to touch, an average of 2.5 mm in length.

Flower description: No flowers or fruit have been observed on the new cultivar to date.

It is claimed:

1. A new and distinct cultivar of *Ilex* plant named 'Spek 02' as herein illustrated and described.

* * * * *